United States Patent [19]

Yoshida

[11] Patent Number: 4,697,076
[45] Date of Patent: Sep. 29, 1987

[54] LIGHTING DEVICE FOR INSPECTING OBJECTS FOR FLAWS

[75] Inventor: Hajime Yoshida, Tokyo, Japan

[73] Assignee: Hajime Industries, Ltd., Tokyo, Japan

[21] Appl. No.: 735,952

[22] Filed: May 20, 1985

[30] Foreign Application Priority Data

May 24, 1984 [JP] Japan ................................ 59-105187

[51] Int. Cl.⁴ ........................ G01N 21/47; B07C 5/342
[52] U.S. Cl. ................................. 250/223 B; 356/240; 209/526
[58] Field of Search .................... 250/223 B; 356/240; 209/526

[56] References Cited

U.S. PATENT DOCUMENTS 4,284,353  8/1981  Yoshida et al. ................. 250/223 B
4,424,441  1/1984  Bieringer et al. ............... 250/223 B

FOREIGN PATENT DOCUMENTS 2042164  9/1980  United Kingdom ............ 250/223 B

Primary Examiner—Edward P. Westin
Assistant Examiner—Charles Wieland
Attorney, Agent, or Firm—Murray Schaffer

[57] ABSTRACT

A lighting device for apparatus detecting flaws in objects having a photoelectric sensor aligned with the object and a processor responsive to the sensor for determining the light received by the sensor. The lighting device includes a ring-shaped lamp and an opaque shield having predetermined light paths controlling the direction of the light from the lamp in a selected direction, so that the light irradiates the object to be inspected in a manner whereby the light is reflected from the object to the sensor only when the object is flawed.

5 Claims, 11 Drawing Figures

LIGHTING DEVICE FOR INSPECTING OBJECTS FOR FLAWS

BACKGROUND OF THE INVENTION

1. Field of the Invention

The present invention relates generally to lighting devices for photo electric flaw detection apparatus and is directed more specifically to a lighting device that uses a ring shaped or circular light source.

2. Description of the Prior Art

Presently, containers made of glass, plastic or the like as the main material have many purposes, such as for use in the bottling of pharmaceuticals, spirits or liquors, cosmetics, beverages and drinks, etc. One problem that rises during the production of such container, particularly bottles, during the distribution and the marketing of the product is the tendency for flaws or breakages to occur at the bottle mouth. Such flaws or breakages at the bottle mouth create problems in capping the bottle, leakage during the filling processes, or during the distribution processes that can ultimately cause breakages of the bottles themselves, or even cause injuries to the users. This is especially significant where use if made of recycled bottles (so-called refillable bottles collected and repeatedly refilled) where the bottles may be subjected to more than several cycles of use. Therefore, the bottle makers or bottlers that wash such bottles and refill the bottles with liquids, conduct manual visual inspection in order to reject any defective bottles, especially those at the bottle mouth.

In recent years, automatic inspection devices for inspecting bottle mouths using optical means, electrical means or the like have been developed to release the manual bottle mouth inspection, and to save labor. These devices, for instance cause the object to be inspected to be illuminated from a light source and the reflected light sensed by photoelectric conversion means such as a photo cell, video camera or the like, so that any abnormal reflection of light as caused by any flaw, crack or damage is detected.

Various lighting arrangements have been proposed for such automatic inspection devices. In one such lighting arrangement, the circular edge portion of the bottle mouth is irradiated (whether this portion is damaged or not) by a ring shaped, i.e., annular lamp such as a circular florescent lamp. An example of the use of this type of lamp in a prior art automatic inspection system is shown in FIG. 1 where the ring shaped lamp 1 is placed generally in a horizontal plane, under which a bottle 2 is placed with its mouth 3 centered along the central axis Y—Y of the lamp 1. The inner diameter of the ring shaped lamp 1 is selected sufficiently larger than the outer diameter of the bottle mouth 3 of bottle 2 and a photoelectric conversion sensor 4 such as a television camera is located to the side of the lamp 1 opposite that of the bottle 2 such that its optical axis is generally aligned with the central axis Y—Y. The sensor 4 receives the light reflected from the bottle mouth 3 and generates corresponding electrical signals which are processed in an otherwise known type inspection section D as a processor (i.e., computer) to determine whether or not a damage or flaw exists on the bottle mouth 3.

The state of the incident light from ring shaped lamp 1 on the bottle mouth 3 in such aforementioned arrangement, as well as the state of the reflected light therefrom is explained in FIGS. 2A, 2B and 2C. In FIGS. 2A, 2B and 2C, the circular lamp 1 amd the sensor 4 are not shown, although the light radiating from the lamp 1 is illustrated by the lines a while their reflections are illustrated by the lines b. Those light rays a extending parallel to or at an acute angle to the axis Y—Y and incident on the curved surface 6 of the circumferential edges of the lip portion 5 of the bottle mouth 3, above the circle shown by a broken line 7 in FIG. 2B, are reflected upward in the direction b and are introduced into the sensor 4 which is located above the bottle mouth 3.

The line 7 lies on the transitional point below which the reflection of light from above or even horizontally is deflected downwardly and thus not capable of incidence on the sensor 4. Generally speaking, the light rays a emitted from the ring-shaped lamp 1 is equally incident on the peripheral edge portion of the bottle mouth 3. The light incident on the mouth 3 above the line 7 when there is no flaw or damage on the bottle mouth 3 is reflected as light b from the surface 6 and enters the sensor 4. In other words, even when there are no abnormalities such as damages or the like on the bottle mouth 3, a part of the light rays from the lamp 1 reflects from the bottle mouth 3 and such reflected light is always introduced into sensor 4. When, however, there is a flaw or damage in the bottle mouth 3, the reflected light becomes scattered and this scattered reflection is introduced into sensor 4 in addition to the aforementioned normal reflected light so that the sensor 4 (and hence the inspection device D) detects an increase or decrease in intensity by which the damage or flaw is recognized. That is to say that in the above mentioned prior art inspection devices, there is an amount of entirely unnecessary reflected light from the bottle mouth 3 always entering the sensor 4, as a result of which the damage or flaw detection sensitivity is low.

Further, depending upon the shape of bottle 2, particularly the shape of the bottle mouth 3, at the inner peripheral edge of bottle mouth 3, there is also an equivalent range of eitherside of the broken line 7, as shown on FIGS. 2B and 2C, causing the incident light near it to also send reflected light into the sensor 4, making the detection more difficult and thereby further lowering the detection sensitivity.

An arrangement attempting to circumvent the above mentioned disadvantages is shown on FIG. 3 wherein a lamp 8 is used that emits a spot like light beam illuminating a small portion of the bottle mouth 3, and the sensor 4 is placed so that it receives only the reflected light from this beam. In this case, unless the bottle mouth 3, which means the bottle itself is rotated, the entire inspection thereof cannot be made, so that an extra bottle rotation device becomes necessary. The arrangement is accompanied by the disadvantage that the inspection takes a longer time to be completed.

OBJECTS AND SUMMARY OF THE INVENTION

Accordingly, an object of the present invention is to provide a lighting device which entirely resolves the defects of the prior art.

According to the present invention, there is provided a lighting device for use with an inspection apparatus having a photoelectric conversion sensor which picks up an image of an object to be inspected and produces an electrical signal and a processor which processes said electrical signal to judge whether said object is good or not, said lighting device comprising:

(a) a ring shape light source for illuminating said object;

(b) a housing made of opaque material and having a ring-shaped space in which said ring-shaped light source is accommodated and a center through-hole through which said sensor picks up an image of said object; and (c) means located between the light source and the object for controlling the direction of light emitted from the ring-shaped light source to said object so that the light is directed in a predetermined direction such that if there is no flaw on said object, no light is reflected from the object to the sensor.

The additional and other objects, freatures and advantages of the present invention will become apparent from the following description taken in conjunction with the accompanying drawings through which the like references designate the same elements and parts.

BRIEF DESCRIPTION OF THE DRAWINGS

FIG. 1 is a schematic diagram showing a prior-art automatic inspection system for a bottle mouth or the like;

DESCRIPTION OF THE PREFERRED EMBODIMENT

Figure 1:
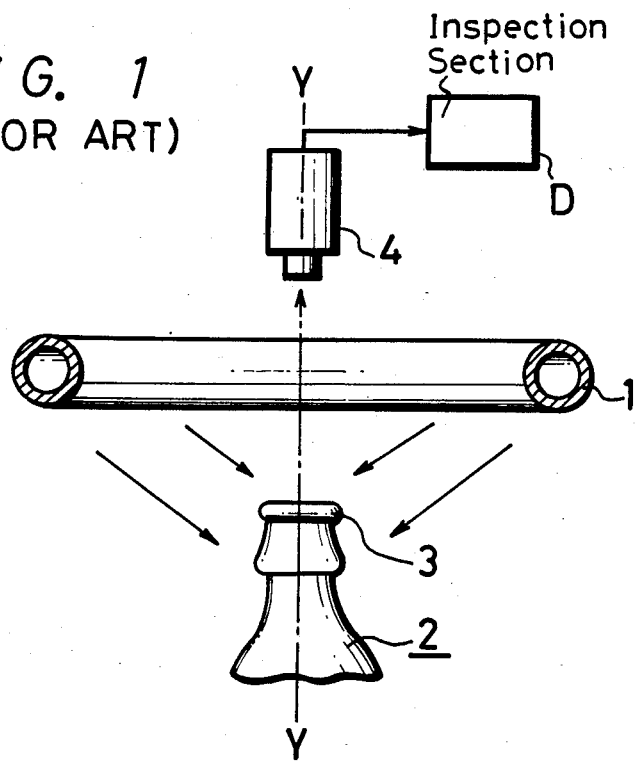
Figure 2A:
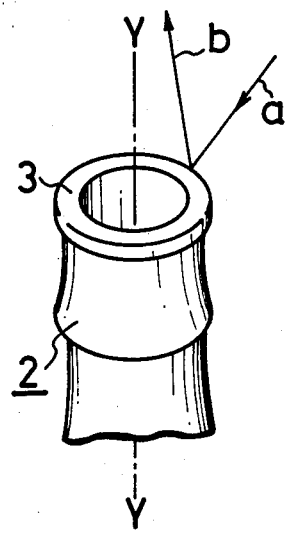
FIGS. 2A, 2B and 2C respectively are a perspective view of a bottle-mouth section, an enlarged side view of a part of the bottle mouth, and a top plan view of the bottle mouth illustrating the incident and reflected light in the prior art system.
Figure 2B:
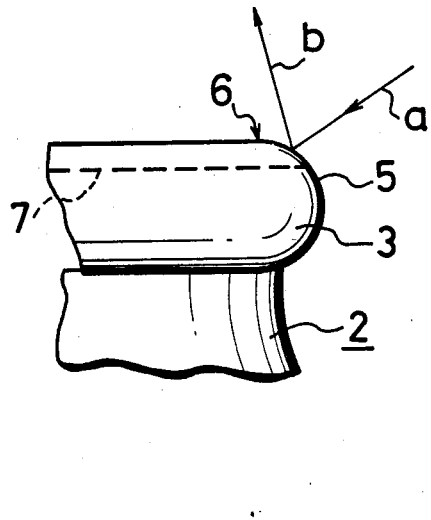
Figure 2C:
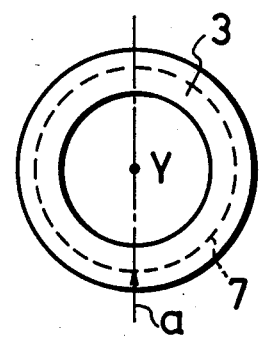
Figure 3:
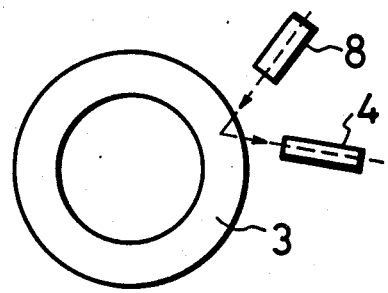
FIG. 3 is a schematic diagram of another example of a prior art automatic inspection system for a bottle mouth.
Figure 4A:
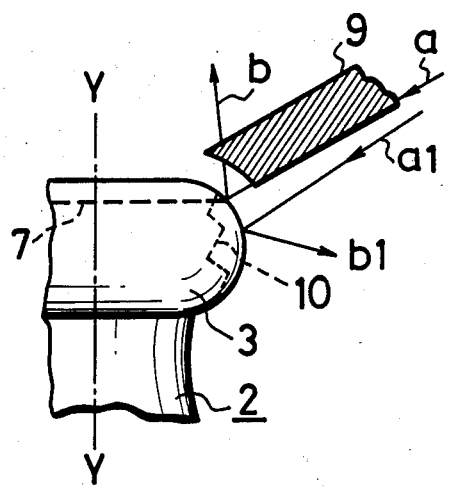
FIGS. 4A and 4B respectively are schematic diagrams of incident and reflected light to explain the basic theory of the present invention.
Figure 4B:
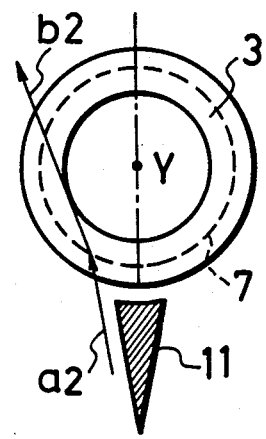

First, the basic theory or principle of the present invention will be explained in reference to FIGS. 4A and 4B. Bearing in mind that while not shown, the ring-shaped light source and sensor would be normally placed as explained in the foregoing so that the reflection b of those rays a directly incident on the line 7, as well as the rays in a narrow band above and to the line 7 and to a lesser degree below the line 7 would normally reach the sensor becoming an unnecessary light not directly related with the sensing or determination of any flaws. The light coming from the light source along the direction shown as a1 so that it is incident below the broken line 7 results in reflection b1, which is directed downwards from the bottle mouth 3 as shown, and it does not normally reach the sensor. To eliminate the unnecessary light reflection, a light shielding means is provided by the present invention, as seen in FIG. 4A, to specifically prevent the passage of the light from the rays a and those above the rays a onto the bottle mouth allowing only the light from only those rays which are lower than the ray a to arrive at the bottle mouth 3, the resultant reflections of which are not directed to the sensor. The shielding means provided need only prevent the passage of the light through the area shown by the cross hatched section 9 in FIG. 4A to prevent light being reflected from a good bottle to the sensor. On the other hand, when there is a damage to the bottle mouth 3, see, for example, as broken line 10 in FIG. 4A, the light that is incident on such damaged surface will be scattered and a part of such scattered light will be reflected into the sensor.

The observations related in FIG. 4A are in conjunction with light rays in the perpendicular direction, that is to say, in the planes that include the central axis Y—Y of the bottle 2, whereas explanations related to the lights in the horizontal direction, which is to say in planes perpendicular to the central axis Y-Y, are explained with reference to FIG. 4B. In this case, the light rays in the direction shown as a2 in FIG. 4B, and incident on an unflawed bottle mouth 3, should have its reflection directed towards the outward circumference in the horizontal plane so that it does not advance upwards towards or reach the sensor. However, when there is a damage or flaw in the bottle mouth 3, the incident light ray a2 will be scattered and, a portion of such scattered light will be reflected upward and reach the sensor. An isosceles triangle area 11 as shown by hatched lines on FIG. 4B designates a shielding area in which the horizontal light from the light source can be prevented from passing onto the bottle mouth 3, in which the incident light would normally be reflected onto the sensor as unnecessary light.

Figure 5A:
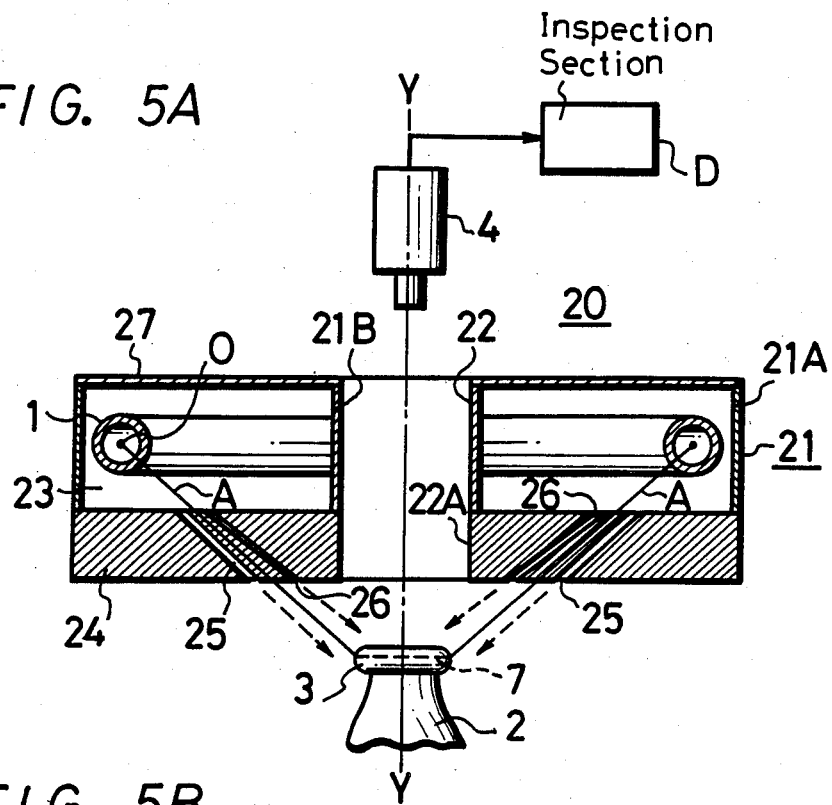
FIG. 5A is a cross-sectional view of a lighting device embodying the present invention.
Figure 5B:
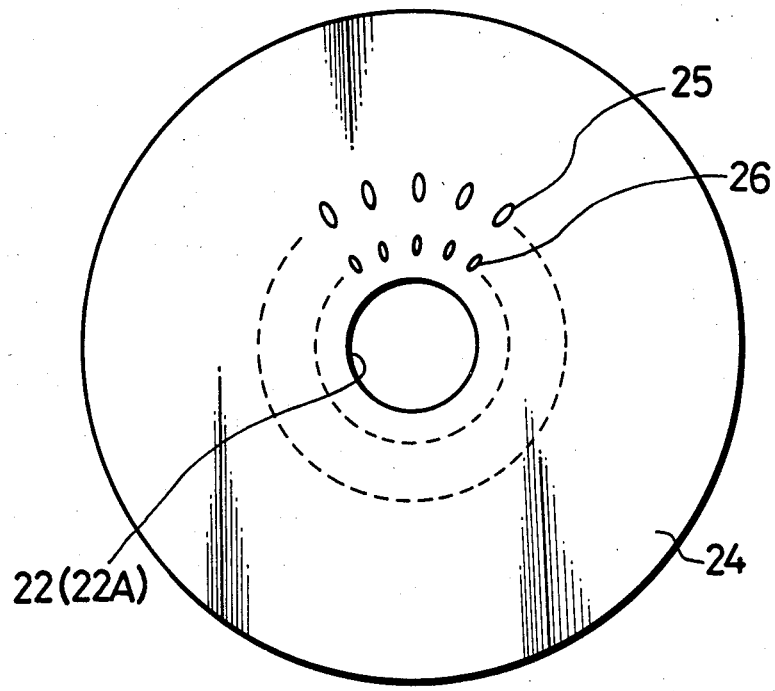
FIG. 5B is a bottom plan view of the lighting device of FIG. 5A.

Turning now to FIGS. 5A and 5B, one example of a lighting device in which the aforementioned basic theory of the present invention is embodied is shown. The references within FIGS. 5A and 5B bearing like numerals to references in FIGS. 1-4 designate the same elements and parts respectively and detail explanations of these will be omitted in order to simplify the text.

The lighting device 20 comprises a cylindrical housing 21 made of opaque material. The housing 21 has an outer cylindrical wall 21A and a concentric inner cylindrical wall 21B, having an inner diameter defining an aperture or through-hole 22 which is selected to be a little larger than the outer diameter of the mouth 3 of bottle 2 being inspected. The inner and outer walls 21A and 21B defines a ring-shaped lamp 1 is properly secured by means, that are not shown on the drawings. A thick ring-shaped bottom wall member 24 made of an opaque material is secured to the lower edge of the circular walls 21A and 21B to enclose the space 23, as a means to control the directions of the light rays from the lamp 1 to the bottle mouth 3. The bottom wall member 24 has a central aperture or through-hole 22A concentrically aligned with the axis Y—Y and having approximately the same diameters as that of the outer and inner cylindrical bodies 21A and 21B.

As shown in FIG. 5A, the housing 21 with the bottom wall member 24 is located between the photoelectric conversion sensor 4 and the bottle 2 so that the central axis of the body 21, and the central axis Y—Y of the lamp 1 are aligned with the optical axis of the sensor 4 as well as the central axis of the mouth 3 of bottle 2. In order to illuminate the bottle mouth 3 in accord with the basic theory of the present invention as explained in reference with FIG. 4, a number of parallel apertures 25 extend angularly through the bottom wall member 24, in paths which form a pair of funnel-like arrays. The apertures 25 pass through the bottom wall 24 ina straight line parallel to and below the straight line A connecting the emmission center O of the lamp 1 and the annular center line 7 on the bottle mouth 3, thus providing a light array in a funnel-like path incident onto the bottle mouth 3, well below the line 7.

In a similar manner, the bottom wall member 24 is provided with a second array of parallel apertures 26 extending from the center O parallel to and above the aforementioned line A so that light does not reach the portions of the bottle mouth 3 above the broken line 7, but irradiates only the top surface portion of bottle mouth 3. In this manner, the light from the lamp 1 is shielded by the wall 24 between the apertures 25 and 26 in the area defined by the cross hatched portion 9 (FIG. 4) and is not incident on the critical area immediately above and below the broken line 7. Although the tile angles of apertures 25 and 26 relative to the horizontal plane of the bottle mouth 3 are not specified, it will be clear, as explained with reference to FIG. 4B, that they are selected so that the light from ring-shaped lamp 1 does not pass through the area 11, as well.

Further, as shown on FIG. 5B, the opening ends of the respective apertures 25 and 26 at the lower surfaces of bottom wall member 24 are each respectively on the same circle of the surface of the wall 24. In the same manner, although not shown in the drawings, the opening ends of the apertures 25, 26 at the top surface of the bottom wall member 24 are respectively on the same circle, these latter circles being of larger diameters than the ones on the lower surface.

Lastly, an opaque cover 27 is mounted on top of the inner and outer cylindrical walls 21a and 21b, respectively, of the housing so as to prevent light from the lamp 1 from being directed upwardly and thus incident on the sensor 4.

The lighting device 20 fulfills the basic theory as aforementioned so that when the light from circular lamp 1 is incident on the bottle mouth 3 it is not reflected onto the sensor 4, unless there are flaws or damages 10 or the like as shown on FIG. 4A at the bottle mouth 3. When such flaws 10 exist, a part of the light scattered therefrom passes through the central through-holes 22A, and is incident on the sensor 4. Thus, with the lighting device 20 according to the present invention, the sensor 4 will not generate any electrical signal when there are no flaws or damage 10 on bottle mouth 3, but generates electric signals only when such flaw or damage exists. Therefore, it is sufficient that the inspection section D that processes the electrical signals from sensor 4 merely detects whether or not the sensor 4 generates an electrical signal. In other words, complicated computer processing equipment is not necessary and the electrical signal from the sensor 4 need only drive an alarm such as sounding a buzzer, lighting a lamp, etc. or generate a signal which drives a defective bottle 2 rejection system (not shown on the drawings). Therefore, the sensor 4 as well as inspection section D may equally be of a simple construction while the defect detection sensitivity is at the same time quite high.

The opening diameters of apertures 25, 26 or their angles relative to the vertical plane and horizontal planes and to the axis Y—Y, can be varied within a wide range while fulfilling the aforementioned basic theory, depending on the size and light intensity of lamp 1, the dimensions of the bottle mouth 3, and the like. In addition, the cross-sectional shape of each of the apertures 25, 26 respectively need not be necessarily round but may be changed into oval or oblong shapes, for example, as long as they are within the range that fulfills the basic theory as explained on FIG. 4. Further, the apertures 25, 26 need not be in 2 rows as it is possible that they may be arranged in an increased or decreased number of rows, depending upon the illumination desired.

Figure 6A:
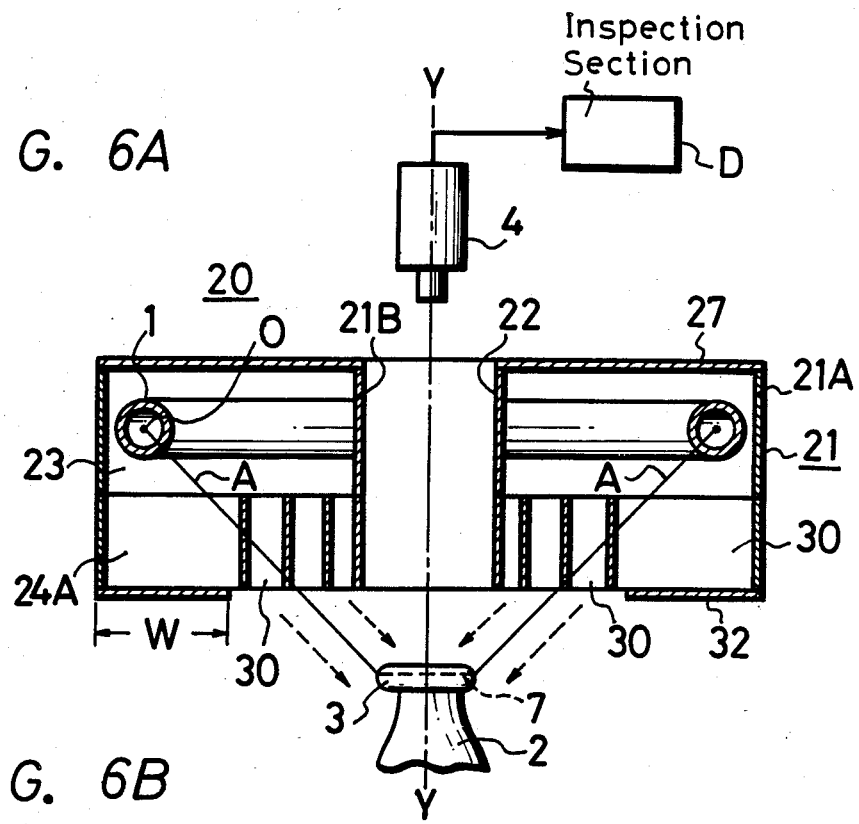
FIGS. 6A and 6B are respectively a cross-sectional view and a bottom view similar to that of FIGS. 5A and 5B of another example embodying the present invention.
Figure 6B:
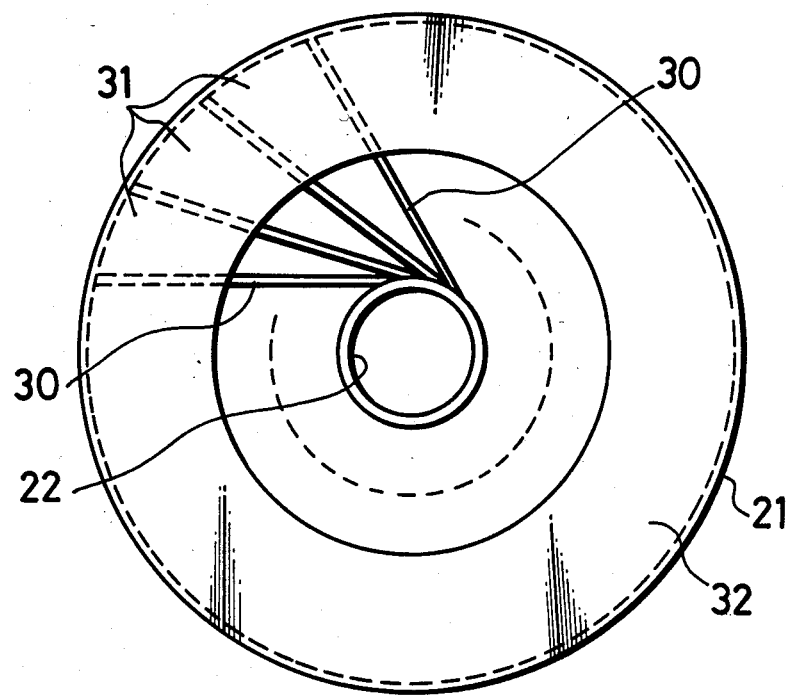

FIGS. 6A and 6B show another example of the present invention where like reference designate the same elements and parts as in FIG. 5 and their detail explanations will be herewith omitted. In FIG. 6, the outer and inner cylindrical bodies 21A and 21B of the housing 21 are respectively extended downwards so that an annular chamber 24A which corresponds to the ring-shape member 24 in FIG. 5 is defined. Within the chamber 24A are located a number of rectangular shaped direction light baffles or control plates 30 made of opaque material. The plates 30 are fit such that one end is secured to the outer surface of the inner cylindrical body 21B, and extended in the radial direction to the outer cylindrical body 21A and the other end is secured to the inner surface of the outer cylindrical body 21A, in a manner that a plurality of spaces 31 defined by neighboring plates 30 are formed each generally of the same triangular shape as shown. A ring shape shield disc 32 made of opaque material is attached as the lower wall to the lower peripheral edge of the outer cylindrical body 21A. The cross-sectional width W of this shield disc 32 is selected so that the inner peripheral edge thereof, generally equals or lies on the circle in which the lower opening aperture 25 shown on FIG. 5 would lie.

FIG. 6 thus illustrates the case where the angular and horizontal light rays from the lamp 1, relative to the center axis Y—Y, is controlled in line with the aforementioned basic theory. Of course, the light direction within the vertical plane to the axis Y—Y is controlled to a certain extent by the ring shape shield plate 32. It is apparent that the example shown in FIG. 6 can provide the same operation and effect as the example shown on FIG. 5.

In both examples of FIGS. 5 and 6, many apertures and directional control plates are used so that the direction of the light from the circular lamp to the inspected object are controlled in accord with the specific basic theory. However, in lieu of the apertures or shield plates, prisms, lenses, optical fibers, mirrors, or other means may be used to control the light direction. Instead of a ring-shaped lamp, a circular fluorescent lamp or a circular stroboscope may be used.

In addition, without departing from the scope of the novel concepts of the present invention, it is apparent that any person skilled in the art may conduct many variations and changes, so that the scope of the invention should be determined by the appended claims only.

I claim as my invention:

1. An apparatus for inspecting objects for flaws having a photoelectric conversion sensor for receiving a reflected image of said object and producing an electric signal indicative thereof and a processor for receiving said electrical signal and judging whether said object is flawed or not, a lighting device for illuminating said object comprising a housing interposed between said sensor and said object, said housing being made of opaque material having a ring-shaped space and a central through hole axially aligned with said sensor and said object, a ring-shaped light source mounted within the ring-shaped space in said housing, and means interposed between said light source and said object for controlling the incidence of light from said light source on said work object, said controlling means comprising an opaque body having a central through-hole and a plurality of light paths disposed thereabout, said controlling means being mounted so that the central through-hole of said controlling means is coincident with the central through-hole of said housing and said light paths are arrayed in a predetermined direction such that the light passing therethrough onto said object will normally not be reflected through the central through-holes onto said sensor and will be reflected onto said sensor only when said object is flawed.

2. The apparatus as claimed in claim 1, wherein the body of said controlling means is ring-shaped and said plurality of light paths comprise a number of apertures formed through said body such that the light emitted from said light source is incident through said apertures on a selected portion of said object.

3. The apparatus as claimed in claim 1, wherein the apertures are grouped into two rows which are respectively arranged in two different frustoconical planes whereby the light from said source is incident on said object at selected portion of said object.

4. The apparatus as claimed in claim 1, wherein said housing is formed of an outer cylindrical member, an inner cylindrical member and a cover connecting said outer and inner cylindrical members about their upper peripheral edges, said ring-shaped light source being located between said cylindrical members at the upper portion thereof, and said controlling means is formed of a number of light shielding plates, each having one end fixed to said inner cylindrical member and its other end to said outer cylindrical member to define a triangular space between adjacent light shielding plates in said housing, and of an opaque ring-shaped plate fixed at the outer peripheral edge thereof to a lower peripheral edge of said outer cylindrical member.

5. A method for inspecting objects for flaws comprising the steps establishing a predetermined direction of reflection of light from the object, illuminating said object with light selectively directed along selected paths so that light is not reflected in the predetermined direction when said object is unflawed and is reflected along said predetermined direction only when said object is flawed, sensing the light reflected only in the predetermined direction and processing the response of said sensor to determine whether the object is flawed or not.

* * * * *